(12) United States Patent  (10) Patent No.: US 7,837,639 B2
Jinright et al.  (45) Date of Patent: Nov. 23, 2010

(54) ADJUSTABLE BRACE FOR CORRECTING A FORWARD LEAN

(76) Inventors: Carey Paul Jinright, 1968 Hillbrook Cir., Auburn, AL (US) 36830; William Lee Jinright, 1661 Old Federal Rd., Shorter, AL (US) 36075

( * ) Notice: Subject to any disclaimer, the term of this patent is extended or adjusted under 35 U.S.C. 154(b) by 238 days.

(21) Appl. No.: 12/209,481

(22) Filed: Sep. 12, 2008

(65) Prior Publication Data

US 2010/0069806 A1  Mar. 18, 2010

(51) Int. Cl.
*A61F 5/00* (2006.01)
(52) U.S. Cl. .......................................... 602/19; 602/16
(58) Field of Classification Search .................. 602/5, 602/19, 32–35, 16; 128/845–846, 98.1, 99.1
See application file for complete search history.

(56) References Cited

U.S. PATENT DOCUMENTS

| | | | | |
|---|---|---|---|---|
| 2,808,050 A | * | 10/1957 | Ward | 602/19 |
| 3,220,407 A | * | 11/1965 | Connelly | 602/19 |
| 4,829,989 A | * | 5/1989 | Deamer et al. | 602/19 |
| 5,176,622 A | * | 1/1993 | Anderson et al. | 602/19 |
| 6,471,665 B1 | * | 10/2002 | Milbourn et al. | 602/19 |
| 2008/0161738 A1 | * | 7/2008 | Giesen | 602/19 |

* cited by examiner

*Primary Examiner*—Michael A. Brown

(57) ABSTRACT

An adjustable brace is provided for correcting a forward lean to obtain an upright position. The brace includes an anterior frame having a chest pad bearing upon a chest area and thigh pads bearing upon thigh areas. The brace has a lumbar pad applied to the lumbar area. The chest pad covers the sternal area substantially from the position of approximately 2" distal to the clavicle bones to about the mid sternum point. The lumbar pad covers the lumbar area from the areas of T-12 to L-5 of the spine. In one embodiment, the frame includes a pubic pad bearing upon a pubic pad. The frame is adjustable in height and width.

27 Claims, 6 Drawing Sheets

ADJUSTABLE BRACE FOR CORRECTING A FORWARD LEAN

FIELD OF THE INVENTION

This invention relates to an adjustable brace. More particularly the present invention relates to an adjustable brace for correcting a forward lean of a body to obtain a more upright position

BACKGROUND OF THE INVENTION

Many spinal conditions can be treated with current spinal orthosis. Kyphosis, for example, is a spinal condition that is observed when a patient may not have the ability to place the thoracic spine into extension. This Kyphosis curvature shows evidence of a forward motion in the upper (thoracic) spine, placing the patient in a "question mark" like posture. This curvature is present in the T-8, T-9 area of the thoracic spine, and continues through to the T-1 vertebrae. This condition can be greatly reduced and supported by a thoracolumbosacral (TLSO) corset or other braces. The reason Kyphosis responds to treatment with these supports is that the lumbar spine remains in a proper position throughout and can be used as an anchor of support. These supports surround the lumbar spine and, with a fourclosure system, apply an anchoring compressive force. This allows the upper spine to be manipulated by the use of metal spinal uprights that work in concert with straps attached to the top of the posterior section. These straps are positioned over the shoulders and under the arms to cross behind the patient and then are Velcro closed in the front to serve as a posterior force to help create a sense of extension in the thoracic spine.

Other spinal presentations include Lordosis, which is the opposite of the above referenced condition. Lordosis mainly affects the lumbar spine and is presented by an extreme forward curve of the lumbar spine. This results in an exaggerated extension of the lumbar spine. This condition is generally treated with a bridging type fit of a lumbar orthosis. Using the top of the sacrum and the base of the thoracic spines the affected area is bridged with a rigid back plate to encourage the spine to reduce its lordotic curve. These conditions are popular and their treatments have been well documented over the years.

Other musculoskeletal deformities and/or abnormalities of the spine have not been documented as well. One of these conditions, which does not have a given medical name, presents the patient with a forward leans as shown in FIG. 1. This lean starts not in the thoracic spine but rather in the L-5 region and the hips. A patient with this condition has a very difficult time standing upright. This posture encourages an exaggerated flexion of the lumbar spine, a reduced forward curve of the thoracic spine and a hyperextension in the cervical spine for the patient to achieve a field of vision. Obviously, it is quite challenging for a patient with this posture to obtain an upright position. This posture generally leads to shortening of the hip flexors and an inability to lift the feet to clear objects due to the inability to overcome the now anterior center of gravity. This center of gravity also leads to excessive knee flexion. With all of the above activities occurring at one time, the patient is placed in an extremely compromised position.

Unfortunately, there is no acceptable, current way to overcome this forward lean posture. With the condition being so low in the spinal column it is not possible with any current products or treatments to produce a counterforce that has an appropriate anchor for correction. What is needed is a product that allows a patient to achieve an upright posture at the lumbar spine region allowing the patient to stand upright throughout the thoracic spines and thereby reduce the hyperextension in the cervical spine.

SUMMARY OF THE INVENTION

The present invention is directed to an adjustable brace for correcting a forward lean to obtain an upright position. The brace comprises an anterior frame having a chest pad bearing upon a chest area and thigh pads bearing upon thigh areas. The brace also includes a lumbar pad applied to the lumbar area. The brace can further include straps for coupling the lumbar pad to the anterior frame at opposite lateral sides thereof. In one embodiment, the anterior frame includes a pubic pad bearing upon a pubic area. In another embodiment, the brace includes shoulder straps for helping to hold the brace in position on a user. The chest pad covers the sternal area substantially from the position of approximately 2" distal to the clavicle bones to about the mid sternum point. The lumbar pad covers the area from the areas of T-12 to L-5 of the spine.

In accordance with one embodiment of the present invention, each pad is heat moldable and coupled to the frame by a bracket. The bracket can be a U-shaped bracket. The pads are removable and the frame is adjustable in length and width. The length adjustment includes knobs on each vertical member of the frame. The width adjustment includes knobs on each horizontal member of the frame.

In accordance with one embodiment of the present invention, the anterior frame is substantially rectangular and continuous. The anterior frame can be made of metal, plastic, steel, aluminum, a polymer material, cable sheath, braided cable, wrapped cable, and combinations thereof. The frame can be tube connected with connection screws. In one embodiment, the frame is one-piece plastic injection molded. In order to allow a user of the brace to sit, when needed, the frame includes a locking mechanism at a location proximal to a hip joint. The locking mechanism can be a release lever.

In accordance with another embodiment of the present invention, an adjustable brace for correcting a forward lean to obtain an upright position is disclosed. The brace comprises an anterior frame having a chest pad bearing upon a chest area, thigh pads bearing upon thigh areas, and a pubic pad bearing upon a pubic area. The brace also includes a lumbar pad applied to the lumbar area. The brace further includes straps coupling the lumbar pad to the anterior frame at opposite lateral sides thereof.

DETAILED DESCRIPTION OF THE PREFERRED EMBODIMENTS

The adjustable brace in accordance with the present invention is specifically designed to achieve an upright posture for patients that suffer from having a forward lean due to spinal weakness. By using the adjustable brace of the present invention, patients that have undergone spinal surgery that later resulted in the onset of this forward lean posture, including others that have had neurological deficits such as Parkinson's Disease which can lead to an inability to achieve proper posture, can maintain proper upright posture. Other patients simply incur much pain in an upright posture such that they succumb to a leaning posture. The support offered by the adjustable brace of the present invention provides enough assistance to allow these patients to maintain a corrected posture.

Figure 1:
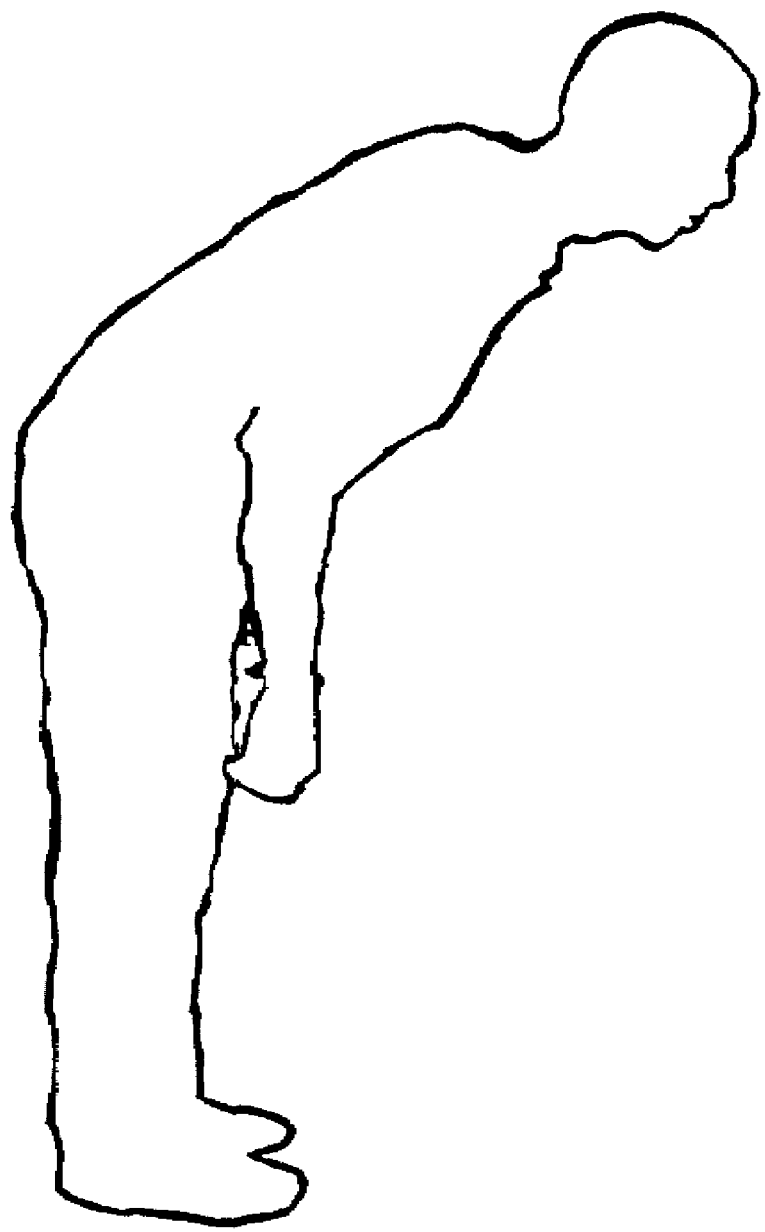
FIG. 1 shows an example of a patient with a forward lean condition.
Figure 2:
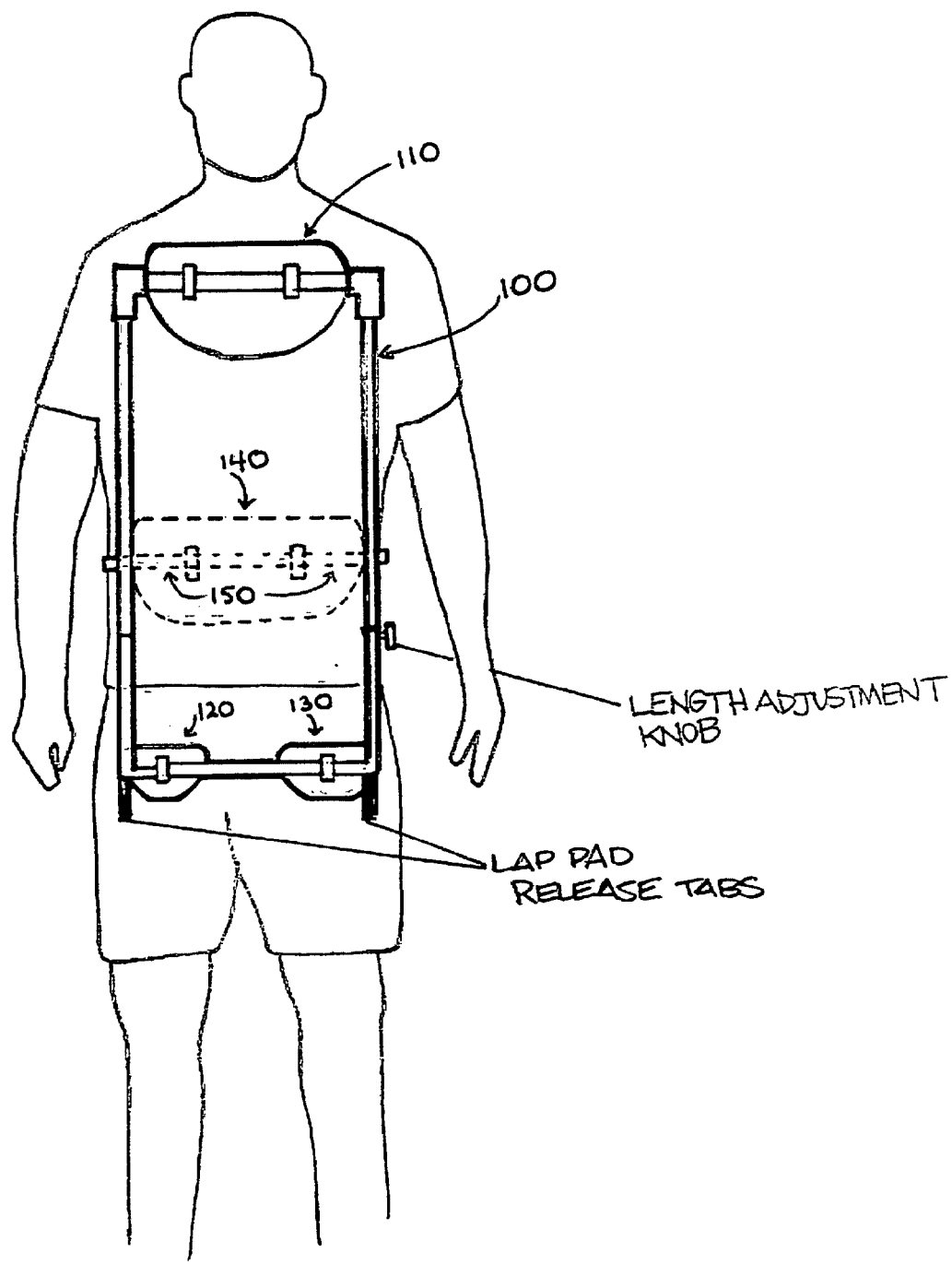
FIG. 2 shows a front view of the adjustable brace as worn on a user, in accordance with one embodiment of the present invention.

FIG. 2 shows a front view of the adjustable brace, as worn on a user, for correcting a forward lean to obtain an upright position, in accordance with one embodiment of the present invention. The figure is merely an example, which should not unduly limit the scope of the claims herein. One of ordinary skill in the art would recognize many other variations, modifications, and alternatives. The brace includes an anterior frame 100 having a chest pad 110 bearing upon a chest area and thigh pads 120 and 130 bearing upon thigh areas. The brace also includes a lumbar pad 140 which is applied to a lumbar area of a patient The lumbar pad 140 is coupled to the anterior frame 100 at opposite lateral sides thereof with straps 150. The straps, which can include a hook-and-loop fabric and attach to both sides of the frame, can be replaced with a flexible waist belt, rivets, snaps, and the like. The straps can be tightened to a comfortable length.

The anterior frame 100 is made of one of the following materials: metal, plastic, steel, aluminum, polymer, cable sheath, foam sheath, flexible sheath, braided cable, wrapped cable and any combination thereof. In one embodiment of the present invention, the anterior frame 100 is substantially rectangular and continuous. In another embodiment, the anterior frame 100 is tube connected with connection screws. The tube connections include both vertical and horizontal members that comprise the anterior frame 100. The anterior frame 100 is adjustable in length and width. The length adjustment includes knobs on each vertical member of the frame 100 and the width adjustment includes knobs on each horizontal member of the frame 100. In some embodiments, switches, buttons, levers, and the like can be used in place of the knobs. In one embodiment, the frame is one-piece plastic injection molded.

The chest pad 100 covers the sternal area substantially from the position of approximately 2" distal to the clavicle bones to about the mid sternum point. The lumbar pad 140 covers the lumbar area from the area of T-12 to L-5 of the spine. In one embodiment, each pad 110, 120, 130 and 140 is coupled to the frame by a bracket. The bracket can be a U-shaped bracket. The pads 110, 120, 130 and 140 should be able to apply considerable pressure without changing shape. The pads 110, 120, 130 and 140 may be tailored individually for the patient. For comfort, the pads 110, 120, 130 and 140 are padded with a foam material, or the like, and provided with a soft outer covering such as leather or simulated leather. In another embodiment, each pad 110, 120, 130 and 140 is heat moldable, removable and lightweight.

The brace of the present invention also allows a patient to sit as needed. Hence, the frame 100 includes a locking release mechanism at a location proximal to the hip joint, wherein the thigh pads 120 and 130 fold up allowing the patient to sit. The locking release mechanism can be a release lever or a push button lock. In general, the locking release mechanism is used only when a patient desires to sit down.

Figure 3:
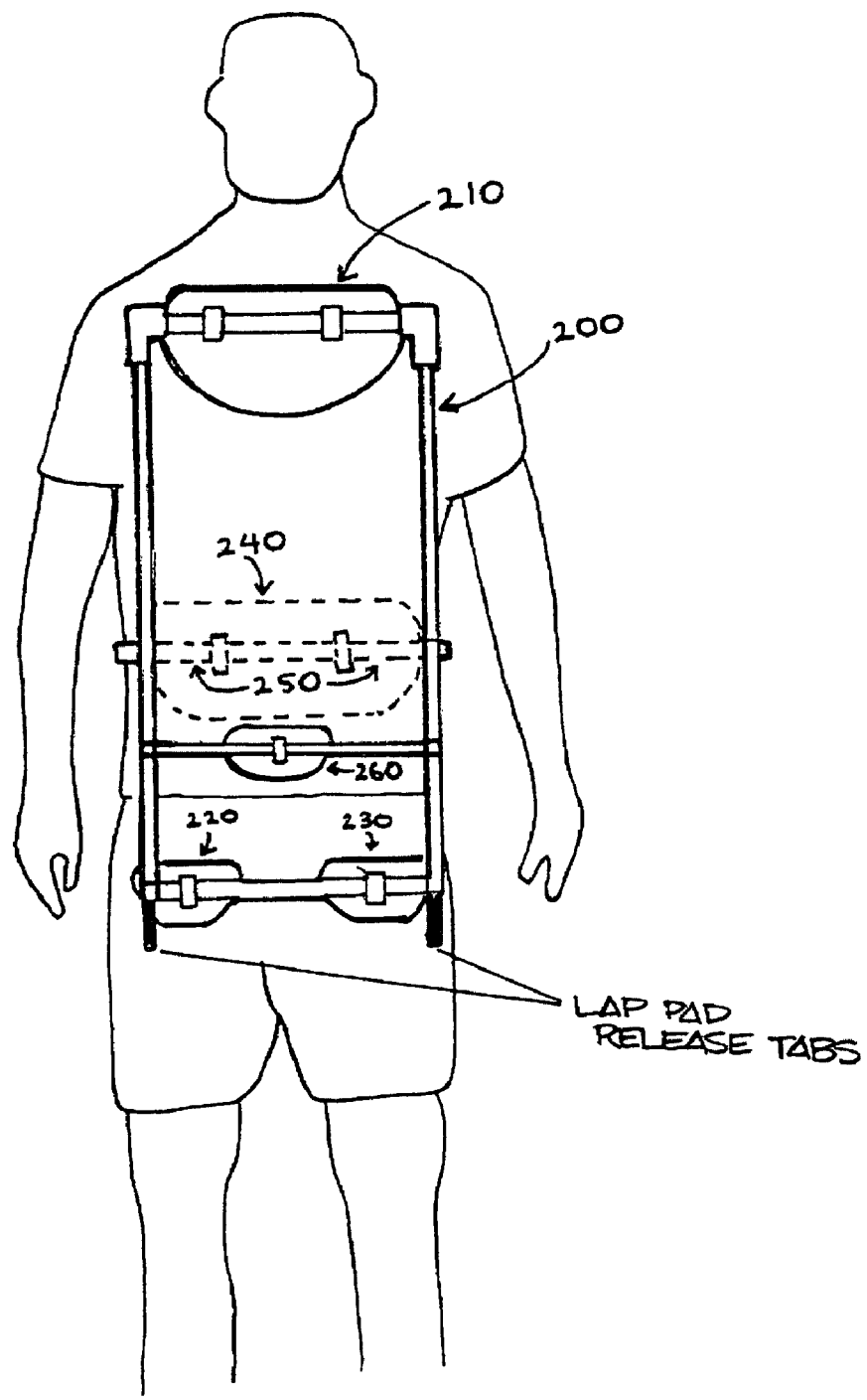
FIG. 3 shows a front view of the adjustable brace as worn on a user in accordance with another embodiment of the present invention.

FIG. 3 shows a front view of the adjustable brace, as worn on a user, for correcting a forward lean to obtain an upright position, in accordance with another embodiment of the present invention. The figure is merely an example, which should not unduly limit the scope of the claims herein. One of ordinary skill in the art would recognize many other variations, modifications, and alternatives. The brace of FIG. 3 comprises an anterior frame 200. The anterior frame 200 includes a chest pad 210 bearing upon a chest area, thigh pads 220 and 230 bearing upon thigh areas, and a pubic pad 260 bearing upon a pubic area. The pubic pad 260 is optional. A lumbar pad 240 is applied to the lumbar area, where in straps 250 couple the lumbar pad to the anterior frame 200 at opposite lateral sides thereof. In one embodiment, the brace includes shoulder straps (not shown) for helping to hold the brace in position on a user.

In one embodiment of the present invention, the lumbar pad 240, the thigh pads 220 and 230, and the pubic pad 260 can have a substantially rectangular shape, whereas the chest pad 210 can have a more rounded or oval shape. Each pad 210, 220, 230, 240, and 260 can be lightweight and concave.

In another embodiment, the anterior frame 200, which can be tube connected at each end, can also be self-adjusting and made of all aluminum construction. In one alternative embodiment, springs (not shown) connect each tube of the anterior frame 200 so that the tubes are resiliently movable with respect to one another, thereby allowing a patient to displace respective ends of the frame away from and towards one another against the bias of the spring.

Figure 4:
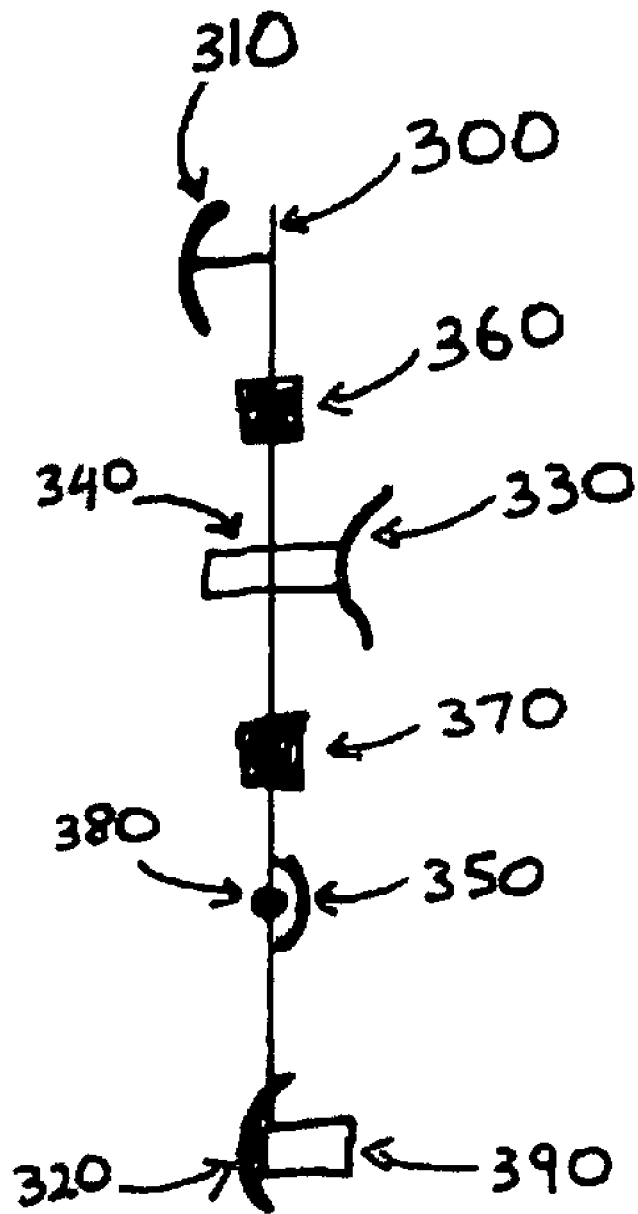
FIG. 4 shows a side cut-away view of the adjustable brace, in accordance with one embodiment of the present invention.

FIG. 4 shows a side cutaway view of the brace, in accordance with one embodiment of the present invention. The figure is merely an example, which should not unduly limit the scope of the claims herein. One of ordinary skill in the art would recognize many other variations, modifications, and alternatives. As shown in the FIG. 4, the brace includes a frame 300 having a chest pad 310, thigh pads 320, and an optional pubic pad 350. In this embodiment, the thigh pads 320 are coupled to the frame 300 by a thigh strap 390. The brace also includes a lumbar pad 330 applied to a lumbar area of a patient. The lumbar pad 330 is coupled the frame 300 via straps 340 at opposite lateral sides thereof. The brace also includes a height adjustment 370 and a width adjustment (not shown). The brace further includes locking release mechanism 380 at a location proximal to a hip joint, wherein the thigh pads 320 fold up allowing a user to sit as needed. The locking mechanism can be a release lever.

Figure 5:
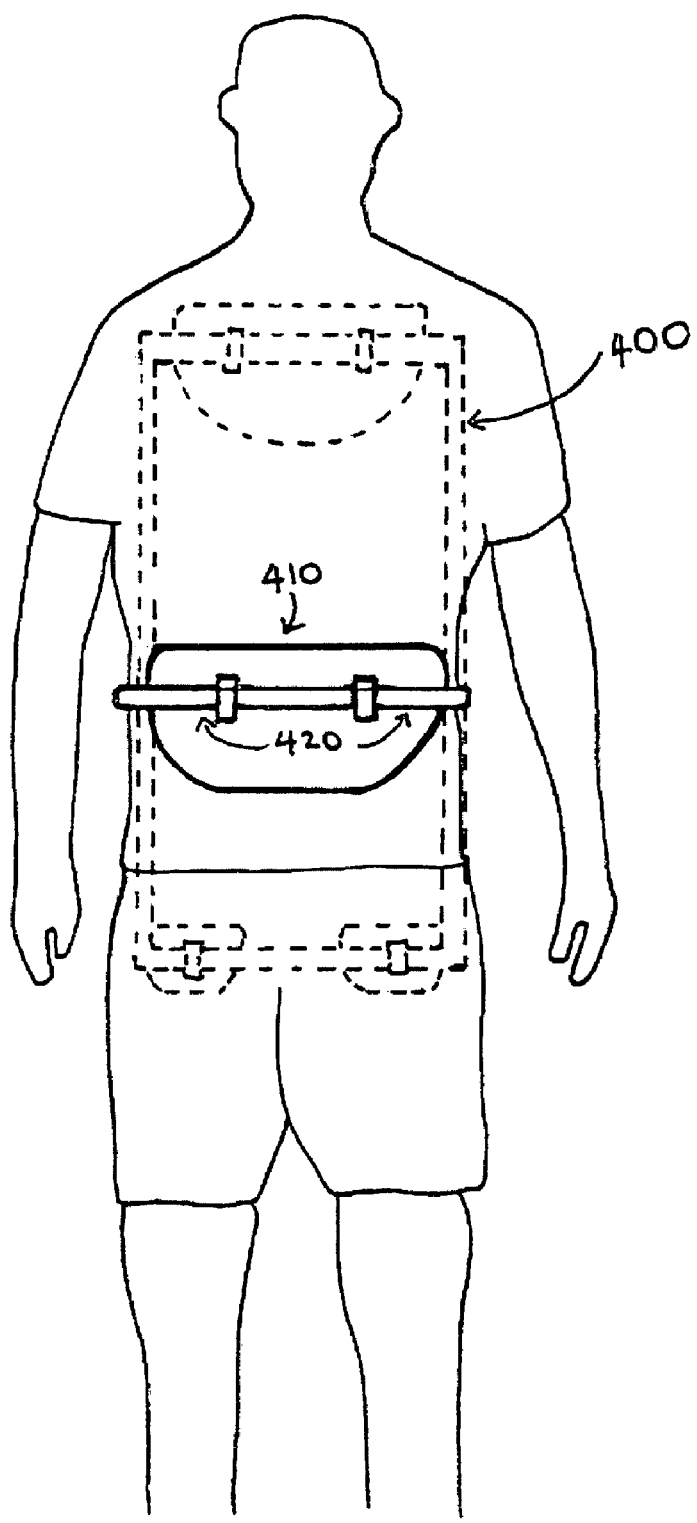
FIG. 5 shows a back view of the adjustable brace, in accordance with one embodiment of the present invention.

FIG. 5 shows a back view of the adjustable brace, in accordance with one embodiment of the present invention. The figure is merely an example, which should not unduly limit the scope of the claims herein. One of ordinary skill in the art would recognize many other variations, modifications, and alternatives. As shown in the FIG. 5, the brace includes a frame 400 and a posterior lumbar pad 410. The lumbar pad 410 is coupled to the frame 400 via straps 420 at opposite lateral sides thereof.

Figure 6:
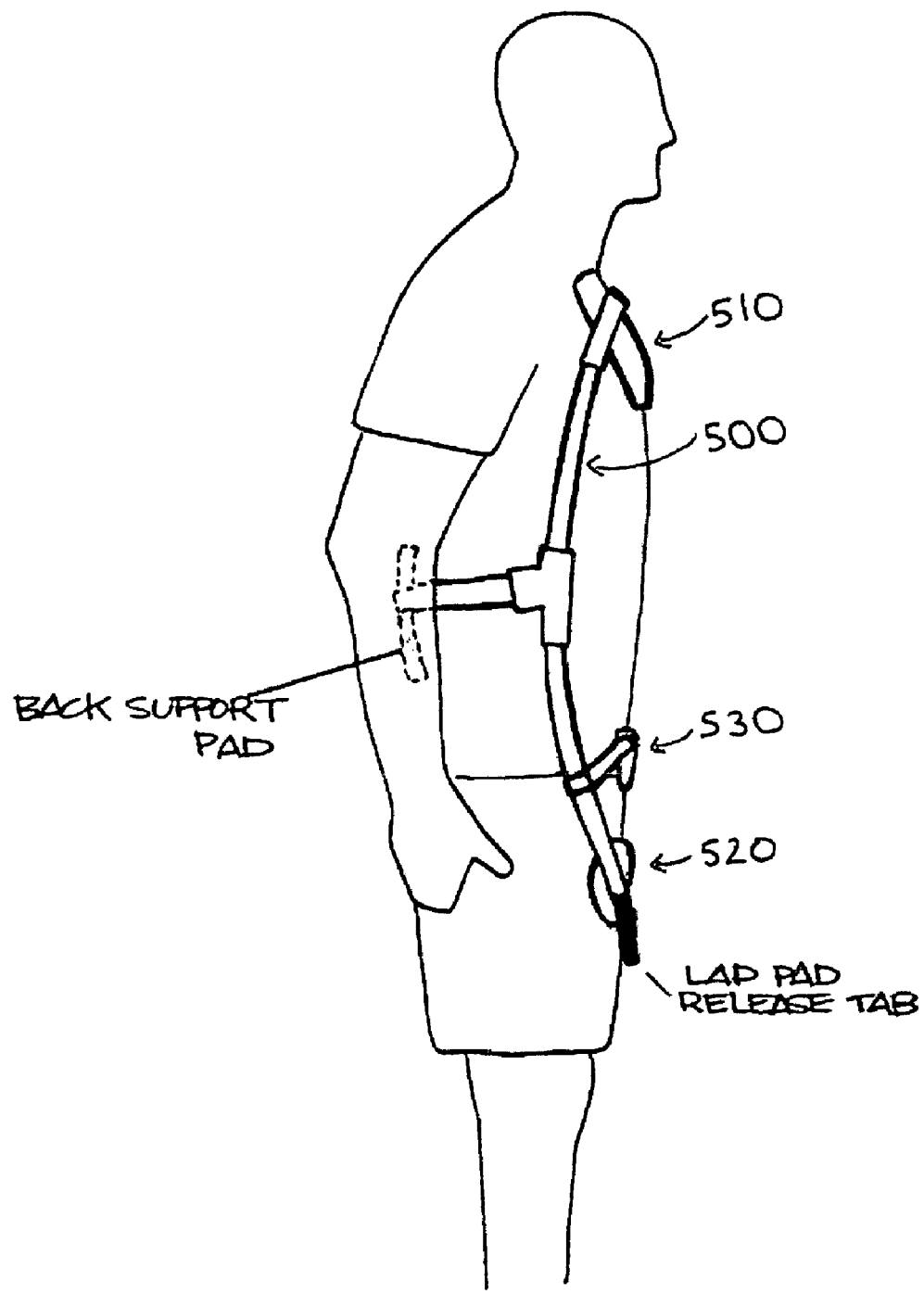
FIG. 6 shows a side view of the adjustable brace, in accordance with one embodiment of the present invention.

FIG. 6 shows a side view of the adjustable brace, in accordance with one embodiment of the present invention. The figure is merely an example, which should not unduly limit the scope of the claims herein. One of ordinary skill in the art would recognize many other variations, modifications, and alternatives. As shown in the FIG. 6, the brace comprises a frame 500. The frame 500 includes a chest pad 510, thigh pads 520, a back support pad, and an optional pubic pad 530. The brace further includes a locking release mechanism or lap release tab at a location proximal to a hip joint, wherein the thigh pads 520 fold up allowing a user to sit as needed.

The present invention has been described in terms of specific embodiments incorporating details to facilitate the understanding of principles of construction and operation of the invention. Such reference herein to specific embodiments and details thereof is not intended to limit the scope of the claims appended hereto. It will be apparent to those skilled in the art that modification may be made in the embodiments chosen for illustration without departing from the spirit and scope of the invention

What is claimed is:

1. An adjustable brace for correcting a forward lean to obtain an upright position, comprising:
    an anterior frame having a chest pad bearing upon a chest area and thigh pads bearing upon thigh areas, wherein the frame includes a locking release mechanism at a location proximal to a hip joint, wherein the thigh pads fold up allowing a user to sit as needed; and
    a lumbar pad applied to the lumbar area.

2. The brace of claim 1 furthering including straps for coupling the lumbar pad to the anterior frame at opposite lateral sides thereof.

3. The brace of claim 1 wherein the anterior frame includes a pubic pad bearing upon a pubic area.

4. The brace of claim 3 wherein each pad is heat moldable.

5. The brace of claim 3 wherein each pad is coupled to the frame by a bracket.

6. The brace of claim 5 wherein the bracket is a U-shaped bracket.

7. The brace of claim 3 wherein the pads are removable.

8. The brace of claim 1 wherein the anterior frame is substantially rectangular and continuous.

9. The brace of claim 8 wherein the frame is tube connected with connection screws.

10. The brace of claim 1 wherein the anterior frame is made of one of the following materials: metal, plastic, steel, aluminum, polymer, cable sheath, braided cable, wrapped cable and combinations thereof.

11. The brace of claim 1 wherein the chest pad covers the sternal area substantially from the position of approximately 2" distal to the clavicle bones to about the mid sternum point.

12. The brace of claim 1 wherein the lumbar pad covers the lumbar area from the areas of T-12 to L-5 of the spine.

13. The brace of claim 1 wherein the locking mechanism is a release lever.

14. The brace of claim 1 wherein the frame is adjustable in length.

15. The brace of claim 14 wherein the length adjustment includes knobs on each vertical member of the frame.

16. The brace of claim 1 wherein the frame is adjustable in width.

17. The brace of claim 16 wherein the width adjustment includes knobs on each horizontal member of the frame.

18. The brace of claim 1 further including shoulder straps for helping to hold the brace in position on a user.

19. An adjustable brace for correcting a forward lean to obtain an upright position, comprising:
    an anterior frame having a chest pad bearing upon a chest area, thigh pads bearing upon thigh areas, and a pubic pad bearing upon a pubic area, wherein the frame includes a locking release mechanism at a location proximal to a hip joint, wherein the thigh pads fold up allowing a user to sit as needed;
    a lumbar pad applied to the lumbar area; and
    straps coupling the lumbar pad to the anterior frame at opposite lateral sides thereof.

20. The brace of claim 19 wherein the anterior frame is made of one of the following materials: metal, plastic, steel, aluminum, polymer, cable sheath, braided cable, wrapped cable and combinations thereof.

21. The brace of claim 19 wherein the chest pad covers the sternal area substantially from the position of approximately 2" distal to the clavicle bones to about the mid sternum point.

22. The brace of claim 19 wherein the lumbar pad covers the lumbar area from the areas of T-12 to L-5 of the spine.

23. The brace of claim 19 wherein the frame is tube connected.

24. The brace of claim 19 wherein each pad is coupled to the frame by a bracket.

25. The brace of claim 19 wherein the frame is adjustable in length and width.

26. The brace of claim 19 wherein the pads are removable.

27. The brace of claim 19 further including shoulder straps for helping to hold the brace in position on a user.

* * * * *